United States Patent
Strauch

(10) Patent No.: US 9,921,196 B2
(45) Date of Patent: Mar. 20, 2018

(54) GAS CHROMATOGRAPH HAVING AN ABSORPTION SPECTROMETER AND METHOD FOR ANALYZING A GAS MIXTURE VIA GAS CHROMATOGRAPHY

(75) Inventor: Piotr Strauch, Rülzheim (DE)

(73) Assignee: Siemens Aktiengesellschaft, Munich (DE)

( * ) Notice: Subject to any disclaimer, the term of this patent is extended or adjusted under 35 U.S.C. 154(b) by 847 days.

(21) Appl. No.: 14/128,920

(22) PCT Filed: Jun. 26, 2012

(86) PCT No.: PCT/EP2012/062302
§ 371 (c)(1),
(2), (4) Date: Feb. 25, 2014

(87) PCT Pub. No.: WO2013/000886
PCT Pub. Date: Jan. 3, 2013

(65) Prior Publication Data
US 2014/0216133 A1    Aug. 7, 2014

(30) Foreign Application Priority Data
Jun. 28, 2011  (DE) .......... 10 2011 078 156

(51) Int. Cl.
*G01N 30/74* (2006.01)
*G01N 21/39* (2006.01)
(Continued)

(52) U.S. Cl.
CPC .......... *G01N 30/74* (2013.01); *G01J 3/42* (2013.01); *G01N 21/39* (2013.01); *G01N 21/3504* (2013.01)

(58) Field of Classification Search
CPC ........................................... G01N 30/74
(Continued)

(56) References Cited

U.S. PATENT DOCUMENTS 3,435,660 A * 4/1969 Sternberg .......... G01F 1/704
                                                    73/23.24
3,897,154 A   7/1975 Hawes
(Continued)

FOREIGN PATENT DOCUMENTS

GB            953952 A      4/1964

OTHER PUBLICATIONS

Zybin et al., Element-selective detection in liquid and gas chromatography by diode laser absorption spectrometry, Jun. 2004, Science Direct, Journal of Chromatography, vol. 1050, Issue 1, pp. 35-44.*
(Continued)

*Primary Examiner* — John Fitzgerald
(74) *Attorney, Agent, or Firm* — Cozen O'Connor

(57) ABSTRACT

A method in which a sample of a gas mixture to be analyzed via gas chromatography is conducted through a chromatographic separating device via a carrier gas, separated components of the gas mixture are subsequently quantitatively determined in an absorption spectrometer having a wavelength-adaptable light source, and in order to increase the speed of analysis and to be able to also determine components that cannot be measured via absorption spectroscopy, the wavelength of the light source can be adapted to an absorption line of the carrier gas, where the individual components of the gas mixture are determined indirectly via a concentration reduction of the carrier gas.

18 Claims, 3 Drawing Sheets

(51) Int. Cl.
*G01J 3/42* (2006.01)
*G01N 21/3504* (2014.01)

(58) Field of Classification Search
USPC .......................... 73/23.37; 356/72, 326, 437
See application file for complete search history.

(56) References Cited

U.S. PATENT DOCUMENTS

| | | | | |
|---|---|---|---|---|
| 4,058,725 | A * | 11/1977 | Aine | G01N 21/1702 250/343 |
| 4,257,257 | A * | 3/1981 | Dairaku | G01N 7/10 73/19.02 |
| 4,654,052 | A * | 3/1987 | Sharp | G01N 30/7293 210/198.2 |
| 6,357,277 | B1 * | 3/2002 | Pigozzo | G01N 30/8665 73/1.06 |
| 7,137,286 | B2 * | 11/2006 | Furukawa | G01N 30/20 73/23.35 |
| 7,511,802 | B2 | 3/2009 | Smith | |
| 8,570,520 | B2 * | 10/2013 | Fleischer | G01N 21/05 356/437 |
| 2003/0015019 | A1 * | 1/2003 | O'Brien | G01N 1/2202 73/23.2 |
| 2005/0109079 | A1 * | 5/2005 | Furukawa | G01N 30/20 73/23.42 |
| 2007/0259440 | A1 * | 11/2007 | Zhou | G01N 21/3504 436/141 |
| 2007/0273882 | A1 * | 11/2007 | Smith | G01N 21/39 356/437 |
| 2008/0311615 | A1 * | 12/2008 | Norton | B01D 15/3833 435/34 |
| 2014/0060152 | A1 * | 3/2014 | Probst | G01N 30/28 73/23.41 |

OTHER PUBLICATIONS

"Element-selective detection in liquid and gas chromatography by diode laser absorption spectrometry"; Zybin A et al, Journal of Chromatography; Elsevier Science Publishers B.V, NL, Bd. 1050, Nr. 1, Sep. 24, 2004; Abstract; Figure 1; p. 39, left column; p. 42, paragraph 4.2; p. 42, left column.

"The use of gas-phase uv spectra in the 168-330-nm wavelength region for analytical purposes. 1. Qualitative measurements"; Lagesson-Andrasko L et al, Analytical Chemistry; American Chemical Society; US; Bd. 70, Nr. 5, Mar. 1, 1998; pp. 819-826; Abstract; Figure 1.

"Indirect detection methods for capillary separations"; E. S. Yeung, W. G. Kuhr, Analytical Chemistry; Bd. 63, Nr. 5, Mar. 1, 1991; pp. 275A-282A; p. 276A, middle column.

\* cited by examiner

GAS CHROMATOGRAPH HAVING AN ABSORPTION SPECTROMETER AND METHOD FOR ANALYZING A GAS MIXTURE VIA GAS CHROMATOGRAPHY

REFERENCE TO RELATED APPLICATIONS

This is a U.S. national stage of application No. PCT/EP2012/062302 filed 26 Jun. 2012. Priority is claimed on German Application No. 10 2011 078 156.0 filed 28 Jun. 2011, the content of which is incorporated herein by reference in its entirety.

BACKGROUND OF THE INVENTION

1. Field of the Invention

The invention relates to a gas chromatograph comprising a chromatographic separating device and a downstream absorption spectrometer, containing a wavelength-tunable light source, for quantitative determination of separated components of a sample of a gas mixture conveyed through the separating device via a carrier gas.

2. Description of the Related Art

The invention furthermore relates to a method for analyzing a gas mixture via gas chromatography, where a sample of the gas mixture is passed through a chromatographic separating device by means of a carrier gas and separated components of the gas mixture are quantitatively determined in a downstream absorption spectrometer having a wavelength-tunable light source.

A gas chromatograph and method are known from U.S. Pat. No. 7,511,802 B2. In the known gas chromatograph and method, after leaving the separating device each individual component is introduced through a switch valve into an analysis cell of the absorption spectrometer. The light of the wavelength-tunable light source is passed through the analysis cell onto a photodetector, the wavelength of the light source being tuned to an absorption line of the component to be determined. The light absorption of the component is dependent on its concentration in the analysis cell, so that the output signal generated by the photodetector is a measure of this concentration. Since the light absorption is very weak, the light beam is conveyed via reflection several times through the analysis cell before it strikes the photodetector. After each determination of a component, the analysis cell is flushed with the carrier gas via the switch valve. Insufficiently separated components may be passed together into the analysis cell and determined there, if they have non-overlapping absorption lines to which the wavelength of the light source can be tuned. In the case of overlapping absorption lines, there is the possibility of separating the components by gas scrubbing and then delivering them individually to the analysis cell. Nitrogen, argon or helium, which are not infrared-active and therefore do not interfere with the absorption spectra of the components to be determined, may be envisioned as the carrier gas.

WO 2008/061949 A1 and WO 2011/026924 A1 respectively disclose an absorption spectrometer in which the analysis cell is configured as a waveguide, in which the gas to be analyzed is contained. The light of the light source is input into the waveguide at one end thereof and output at the other end onto the photodetector. The light is guided by reflection in the optionally internally mirrored waveguide, so that the waveguide may be curved and therefore formed as a hollow fiber. In order to reduce artefacts, such as interference, the waveguide may be set in vibration. The advantage of this known absorption spectrometer resides in the small measurement volume and the long optical measurement path.

In connection with the known determination via absorption spectrometry of components previously separated via gas chromatography, as already mentioned above, the following problems arise:

With wavelength-tunable light sources commercially available at present, generally lasers or laser diodes, only a very restricted number of gas components can be determined; for example, noble gases or nitrogen in principle and higher hydrocarbons in practice cannot be measured.

The tuning of the light source to the absorption lines of the various components is elaborate and time-consuming.

The carrier gases used are expensive.

SUMMARY OF THE INVENTION

It is therefore an object of the invention to provide a gas chromatograph having an absorption spectrometer and method for analyzing a gas mixture via gas chromatography that resolves the foregoing problems.

This and other objects and advantages are achieved in accordance with the invention by a gas chromatograph and method for analyzing a gas mixture via gas chromatography in which the wavelength of the light source is tuned to an absorption line of the carrier gas, the quantitative determination of the individual components of the gas mixture being performed indirectly via a concentration reduction of the carrier gas.

Since the concentrations of the individual components are measured not directly but indirectly, by means of the concentration reduction of the carrier gas due to the separated components, it is also possible to determine components that themselves cannot be measured directly via absorption spectrometry, for example, because their absorption lines lie outside the tunable wavelength range of the absorption spectrometer used. Light sources, generally lasers or laser diodes, with wavelengths tunable in the (near) infrared range are conventionally used. If the absorption line of the carrier gas, to which the light source is tuned, overlaps with the absorption spectra of individual components, the determination of these components can be referenced simply to a determination, via absorption spectrometry, of the carrier gas in the absence of components of the gas mixture, i.e., for example, between two successive and sufficiently separated components or when flushing the gas chromatograph with the carrier gas. If individual components cannot be separated sufficiently, the wavelength of the light source may additionally or alternatively be tuned to an absorption line of the relevant component. Apart from this, the measurement of the components is performed very simply and therefore also rapidly, because the light source only needs to be tuned to a single absorption line, i.e., that of the carrier gas. Once the light source has been tuned to a selected absorption line of the carrier gas, this wavelength only needs to be modulated in a narrow range around the central wavelength of the absorption line, in order to stabilize the light source to the middle of the absorption line.

Economical gases, such as oxygen, carbon dioxide or methane, with a suitable absorption line may in particular be used as the carrier gas. The latter may be a single gas or a carrier gas mixture, comprising a gas component which has a suitable absorption line and whose concentration in the carrier gas mixture is constant at least during each measurement cycle. For this reason, owing to the constant oxygen content of about 21%, air may particularly advantageously be used as the carrier gas. Moreover, the carrier gas selected can also be used when it is itself intended to be measured as a component of the gas mixture to be analyzed. In this case, for determination of the component equivalent to the carrier gas, a further, unseparated sample of the gas mixture may be introduced into the absorption spectrometer instead of the carrier gas coming from the separating device with the separated components. To this end, a controllable switch valve between the separating device and the absorption spectrometer is merely necessary.

Preferably, the absorption spectrometer has a waveguide through which the carrier gas with the separated components flows, the light source and a photodetector being arranged with respect to the waveguide such that the light of the light source strikes the photodetector after shining through the waveguide in the longitudinal direction of the latter. Regarding details and possible configurations of the structure of the waveguide and of the input and output of the light and of the carrier gas, respectively into and out of the waveguide, reference is made to WO 2008/061949 A1 and WO 2011/026924 A1, which were mentioned above. In contrast to the gas chromatograph known from U.S. Pat. No. 7,511,802 B2, the carrier gas with the separated components is preferably conveyed continuously through the waveguide, the internal diameter of which preferably corresponds at least approximately to the internal diameter of the separating device. The separated components then travel through the waveguide without perturbation of their shape (peak) and are sampled by the absorption spectrometer. The sampling in this case corresponds to a short-term integral over the peak with a window length corresponding to the length section of the waveguide through which the carrier gas with the separated components flows, and through which the light simultaneously shines. The profile of the peak can be detected from the variation of the output signal generated by the photodetector as a function of time. If, according to an advantageous embodiment of the invention, the length section of the waveguide through which the carrier gas with the separated components flows, and through which the light simultaneously shines, corresponds at least approximately to the greatest peak width to be expected for the separated components, then the peak area proportional to the concentration of the component can be determined with a single measurement as soon as the peak lies fully within the waveguide.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will be explained below with reference to the figures of the drawing with the aid of exemplary embodiments in which.

DETAILED DESCRIPTION OF THE PREFERRED EMBODIMENTS

Figure 1:
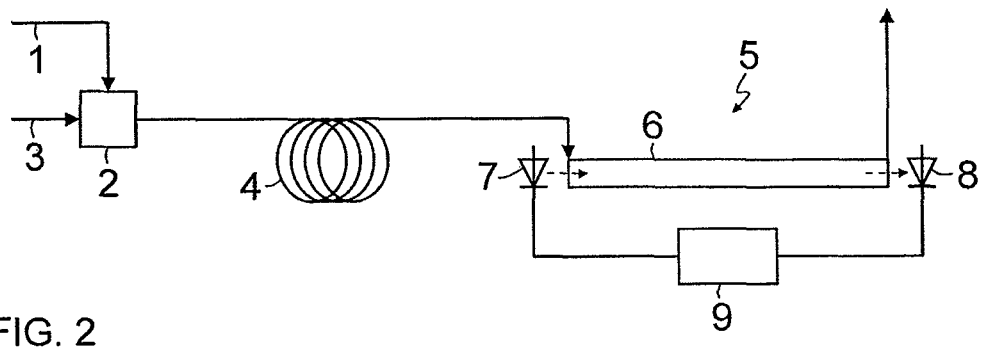
FIG. 1 shows a schematic representation of the gas chromatograph in accordance with the invention.

FIG. 1 shows a process gas chromatograph for analyzing a gas mixture 1, which is delivered to a dosing device 2 after extraction from an industrial process. The dosing device 2 is used to introduce a predetermined dosing amount of the gas mixture 1 as a short and sharply delimited sample bolus, referred to below as the sample, into a carrier gas flow 3 at a predetermined time and deliver it to a separating device 4 as a separating column or separating column circuit. The separating device 4 separates the components of the gas mixture 1, which are contained in the sample, according to their retention times, so that the components appear successively at the exit of the separating device 4.

An absorption spectrometer 5 for detection and quantitative determination of the separated components is arranged at the exit of the separating device 4. To this end, the absorption spectrometer 5 has an analysis cell 6 through which the carrier gas 3 with the separated components flows, and through which the light of a wavelength-tunable light source 7, such as a laser diode, is passed onto a photodetector 8. A control and evaluation device 9 controls the light source 7 and evaluates the output signal delivered by the photodetector 8.

The carrier gas 3 is a single gas, or a carrier gas mixture having a gas component in a concentration which is constant at least during the measurement cycle, such as air, or atmospheric oxygen. The wavelength of the light source 7 is tuned to an absorption line of the carrier gas 3, or of the gas component in the carrier gas mixture, so that the absorption spectrometer 5 measures the concentrations of the separated components indirectly via the concentration reduction of the carrier gas 3 due to these components. It is therefore also possible to determine components of the gas mixture 1 whose absorption lines lie outside the tunable wavelength range of the light source 7.

Figure 2:
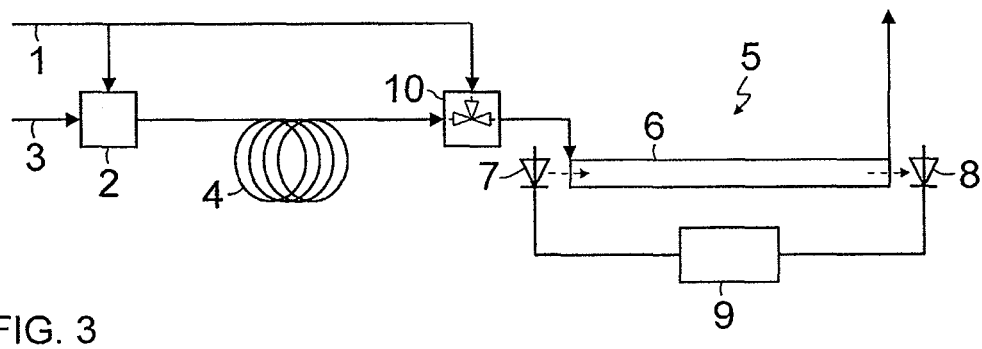
FIG. 2 shows a modified exemplary embodiment of the gas chromatograph shown in FIG. 1.

FIG. 2 shows an extension of the gas chromatograph with a controllable switch valve 10 between the separating device 4 and the absorption spectrometer 5. If the gas mixture 1 contains a component that is identical to the carrier gas 3 (or the aforementioned component of the carrier gas mixture), here for example oxygen, then for the quantitative determination of this component the gas mixture 1 is delivered through the switch valve 10 directly, i.e., without separation via chromatography, to the absorption spectrometer 5 until the analysis cell 6 is fully filled with the gas mixture 1.

Figure 3:
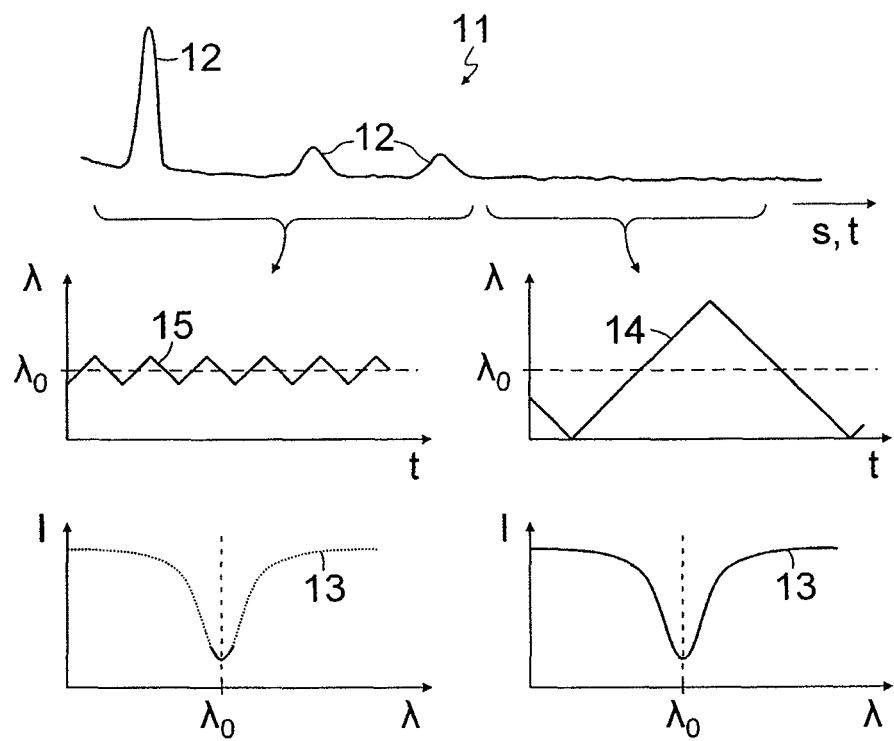
FIG. 3 shows a chromatogram and examples of the driving of the wavelength-tunable light source.

FIG. 3 shows, in the upper part, an example of a chromatogram 11 in which the components of the gas mixture 1, which are separated as a function of time and position, appear as peaks 12. The areas under the peaks 12 respectively correspond to the concentrations of the associated components. The lower part of the figure shows the absorption line 13 of the carrier gas 3, to which the wavelength $\lambda$ of the light source 7 is tuned. The absorption line 13 here reflects the wavelength-dependent intensity I of the light striking the photodetector 8, i.e., not absorbed by the carrier gas 3. When there are no components of the gas mixture 1 in the analysis cell 6 of the absorption spectrometer 5, i.e., here in the right-hand part of the chromatogram 11, or when the chromatograph, or the analysis cell 6, is flushed with the carrier gas 3, the wavelength λ of the light source 7 is modulated over a relatively large wavelength range (modulation function 14) in order to find the central wavelength $\lambda_0$ of the absorption line 13. Once the light source 7 has been tuned to the central wavelength $\lambda_0$ of the absorption line 13, the wavelength λ only needs to be modulated in a narrow range around the central wavelength λ (modulation function 15) to stabilize the light source 7 to the middle of the absorption line 13. Owing to the smaller wavelength range to be sampled, the sampling time for the modulation function 15 with the small amplitude is substantially shorter than for the modulation function 14 with the large amplitude. The determination of the components of the gas mixture 1 can therefore be performed with a high speed and therefore high resolution as a function of time or position, because the light source 7 only needs to be stabilized to the selected absorption line 13 of the carrier gas 3 during the analysis of all components of the gas mixture 1 that are separated via gas chromatography.

Figure 4:
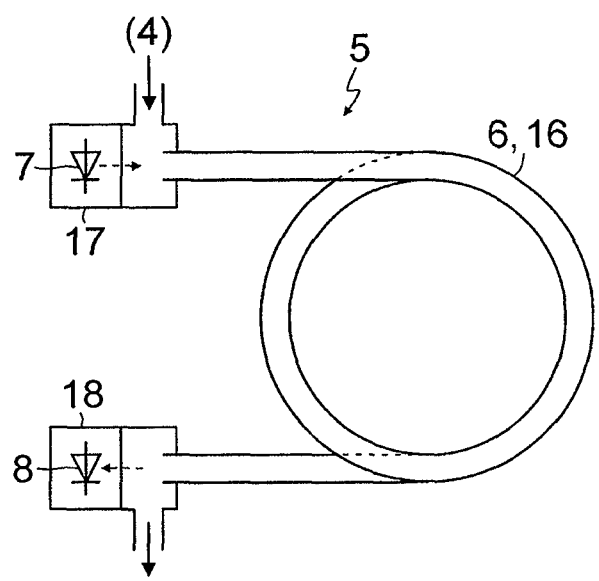
FIG. 4 shows an exemplary embodiment of the absorption spectrometer having a waveguide as the analysis cell.

FIG. 4 shows an exemplary embodiment of the absorption spectrometer 5, in which the analysis cell 6 is formed as a waveguide 16, in particular as a flexible hollow fiber. The light of the light source 7 is input into one end of the waveguide 16 and conveyed therein by reflection on the preferably mirrored inner wall to the photodetector 8 at the other end of the waveguide 16. At the same time, the carrier gas 3 coming from the separating device 4 with the separated components of the gas mixture 1 flows through the waveguide 16. The light source 7 and/or the photodetector 8 may be arranged in chambers 17, 18 filled with neutral gas or the carrier gas 3. The length of the waveguide 16 is dimensioned such that it corresponds approximately to the greatest peak width to be expected for the separated components. The position of the peak 12 (FIG. 3) of a component entering the waveguide 16 can be detected from the variation of the output signal generated by the photodetector 8 as a function of time. As soon as the peak 12 lies fully in the waveguide 16, the peak area proportional to the concentration of the component can be determined with a single measurement.

Figure 5:
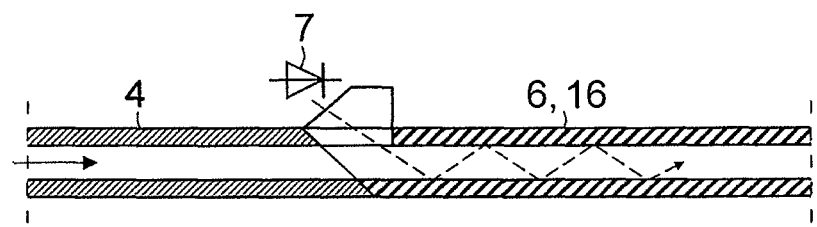
FIG. 5 shows an example of the input of light into the waveguide.

FIG. 5 shows a schematic representation of an example of an input, taking place from the side, of the light of the light source 7 into the waveguide 16. At the position of the light input, the lateral surface of the waveguide 16 is transparent. The separating device 4 merges directly into the waveguide 16, the internal diameter of which corresponds at least approximately to the internal diameter of the separating device 4. The effect achieved by this is that the peaks 12 (FIG. 3) of the separated components can enter the waveguide 16 unperturbed and be measured there.

Figure 6:
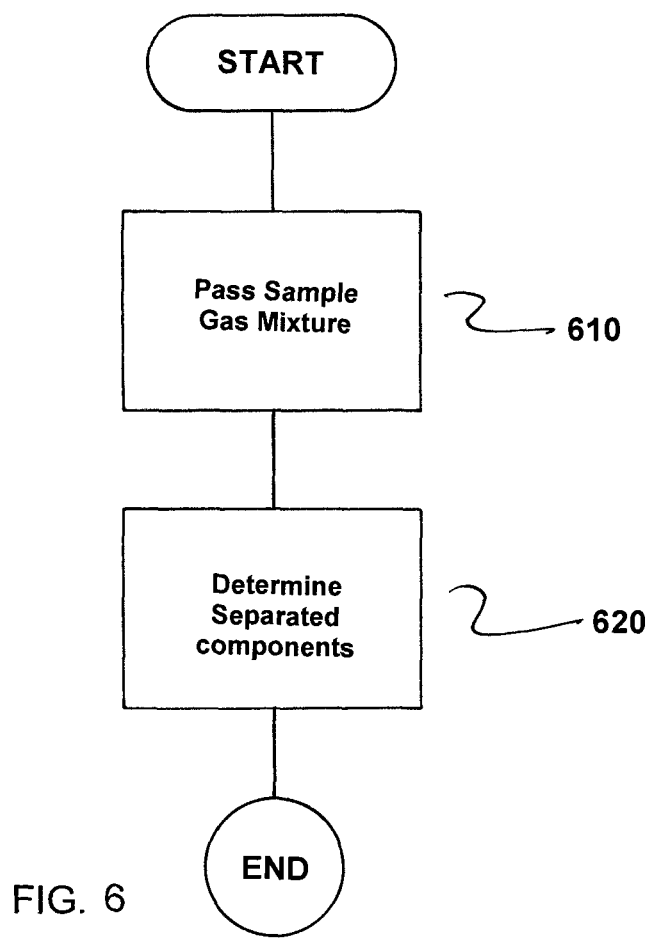
FIG. 6 is a flowchart of the method in accordance with the invention.

FIG. 6 is a flowchart of a method for analyzing a gas mixture via gas chromatography. The method comprises passing a sample of the gas mixture through a chromatographic separating device via a carrier gas, as indicated in step 610. Quantitatively separated components of the gas mixture in a downstream absorption spectrometer having a wavelength-tunable light source are then determined, as indicated in step 620. Here, the wavelength of the light source is tuned to an absorption line of the carrier gas, and the quantitative determination of individual components of the gas mixture is performed indirectly via a concentration reduction of the carrier gas While there have been shown, described and pointed out fundamental novel features of the invention as applied to a preferred embodiment thereof, it will be understood that various omissions and substitutions and changes in the form and details of the methods described and the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A gas chromatograph comprising:
   a chromatographic separating device;
   an absorption spectrometer arranged downstream of the chromatographic separating device;
   a wavelength-tunable light source; and
   a carrier gas, the gas chromatograph quantitatively determining separated components of a sample of a gas mixture conveyed through the chromatographic separating device via the carrier gas;
   wherein a wavelength of the light source is tuned to an absorption line of the carrier gas; and
   wherein the absorption spectrometer performs a quantitative determination of individual components of the gas mixture indirectly via a concentration reduction of the carrier gas.

2. The gas chromatograph as claimed in claim 1, further comprising:
   a controllable switchover valve arranged between the separating device and the absorption spectrometer for selective introduction of the carrier gas coming from the chromatographic separating device with one of (i) the separated components of the gas mixture into the absorption spectrometer and (ii) a further, unseparated sample of the gas mixture into the absorption spectrometer.

3. The gas chromatograph as claimed in claim 1, wherein the carrier gas comprises a carrier gas mixture having a gas component whose concentration in the carrier gas mixture is constant at least during a measurement, and wherein the wavelength of the light source is tuned to an absorption line of this gas component.

4. The gas chromatograph as claimed in claim 3, wherein the absorption spectrometer includes a hollow fiber through which the carrier gas with the separated components flows, and wherein the light source and a photodetector are arranged with respect to the hollow fiber such that light of the light source strikes the photodetector after shining through the hollow fiber in a longitudinal direction of the waveguide.

5. The gas chromatograph as claimed in claim 1, wherein the absorption spectrometer includes a hollow fiber through which the carrier gas with the separated components flows, and wherein the light source and a photodetector are arranged with respect to the hollow fiber such that light of the light source strikes the photodetector after shining through the hollow fiber in a longitudinal direction of the waveguide.

6. The gas chromatograph as claimed in claim 5, wherein the hollow fiber is internally mirrored.

7. The gas chromatograph as claimed in claim 5, wherein a length of the hollow fiber is dimensioned such that a length section of the hollow fiber through which the carrier gas with the separated components flows, and through which the light simultaneously shines, substantially corresponds to a greatest peak width to be expected for the separated components.

8. The gas chromatograph as claimed in claim 5, wherein the hollow fiber has an internal diameter which substantially corresponds to an internal diameter of the chromatographic separating device.

9. The gas chromatograph as claimed in claim 8, wherein a length of the hollow fiber is dimensioned such that a length section of the waveguide through which the carrier gas with the separated components flows, and through which the light simultaneously shines, substantially corresponds to a greatest peak width to be expected for the separated components.

10. A method for analyzing a gas mixture via gas chromatography, comprising:
    passing a sample of the gas mixture through a chromatographic separating device via a carrier gas; and
    determining quantitatively separated components of the gas mixture in a downstream absorption spectrometer having a wavelength-tunable light source;
    wherein a wavelength of the light source is tuned to an absorption line of the carrier gas;
    wherein the quantitative determination of individual components of the gas mixture is performed indirectly via a concentration reduction of the carrier gas.

11. The method as claimed in claim 10, further comprising:
    continually conveying the carrier gas with the separated components through a hollow fiber in the absorption spectrometer; and
    passing the light of the light source through the hollow fiber in a longitudinal direction of the hollow fiber onto a photodetector.

12. The method as claimed in claim 10, wherein the wavelength of the light source is additionally or alternatively tuned to an absorption line of a relevant component to determine at least one but not all components.

13. The method as claimed in claim 10, further comprising:
    introducing a further, unseparated sample of the gas mixture into the absorption spectrometer instead of the carrier gas coming from the separating device with the separated components to determine a component, equivalent to the carrier gas, of the gas mixture to be analyzed.

14. The method as claimed in claim 10, wherein a carrier gas mixture having a gas component whose concentration in the carrier gas mixture is constant at least during a measurement is used as the carrier gas; and
    wherein the wavelength of the light source is tuned to an absorption line of this gas component.

15. The method as claimed in claim 14, wherein light absorption of the carrier gas is measured during absence of components of the gas mixture in the absorption spectrometer, and is used for referencing the quantitative determination of the components.

16. The method as claimed in claim 14, further comprising:
    continually conveying the carrier gas with the separated components through a hollow fiber in the absorption spectrometer; and
    passing the light of the light source through the hollow fiber in a longitudinal direction of the waveguide onto a photodetector.

17. The method as claimed in claim 10, wherein light absorption of the carrier gas is measured during absence of components of the gas mixture in the absorption spectrometer, and is used for referencing the quantitative determination of the components.

18. The method as claimed in claim 17, further comprising:
    continually conveying the carrier gas with the separated components through a hollow fiber in the absorption spectrometer; and
    passing the light of the light source through the waveguide in a longitudinal direction of the hollow fiber onto a photodetector.

* * * * *